US00PP21623P2

(12) United States Plant Patent
Sakazaki

(10) Patent No.: US PP21,623 P2
(45) Date of Patent: Jan. 11, 2011

(54) *PHLOX* PLANT NAMED 'USPLX50304'

(50) Latin Name: *Phlox hybrida*
Varietal Denomination: USPLX50304

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/653,199

(22) Filed: Dec. 9, 2009

(51) Int. Cl.
*A01H 5/00* (2006.01)

(52) U.S. Cl. ..... Plt./320

(58) Field of Classification Search ..... Plt./320
See application file for complete search history.

*Primary Examiner*—Annette H Para
(74) *Attorney, Agent, or Firm*—C. A. Whealy

(57) ABSTRACT

A new and distinct cultivar of *Phlox* plant named 'USPLX50304', characterized by its upright, outwardly spreading and mounding plant form; vigorous growth habit; freely branching habit and short internodes; dense and busy plant habit; freely and continuous flowering habit; bright purple violet-colored flowers; relatively tolerant to high temperatures; and relatively resistant to Powdery Mildew.

1 Drawing Sheet

Botanical designation: *Phlox hybrida.*
Cultivar denomination: 'USPLX50304'.

BACKGROUND OF THE INVENTION

The present invention relates to a new and distinct cultivar of *Phlox* plant, botanically known as *Phlox hybrida* and hereinafter referred to by the name 'USPLX50304'.

The new *Phlox* plant is a product of a planned breeding program conducted by the Inventor in Higashiomi, Shiga, Japan and Bonsall, Calif. The objective of the breeding program is to create new uniformly mounding *Phlox* plants with unique flower color and resistance to Powdery Mildew.

The new *Phlox* plant originated from a cross-pollination made by the Inventor on Jun. 12, 2005 in Higashiomi, Shiga, Japan of an unnamed selection of *Phlox glabriflora,* not patented, as the female, or seed, parent with an unnamed seedling selection of *Phlox hybrida,* not patented, as the male, or pollen, parent. The new *Phlox* plant was discovered and selected by the Inventor as a single flowering plant within the progeny of the stated cross-pollination in a controlled environment in Bonsall, Calif. on Jul. 6, 2006.

Asexual reproduction of the new *Phlox* plant by cuttings in a controlled environment in Bonsall, Calif. since Jul. 10, 2006, has shown that the unique features of this new *Phlox* plant are stable and reproduced true to type in successive generations.

SUMMARY OF THE INVENTION

Plants of the new *Phlox* plant have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USPLX50304'. These characteristics in combination distinguish 'USPLX50304' as a new and distinct cultivar of *Phlox:*

1. Upright, outwardly spreading and mounding plant form.
2. Vigorous growth habit.

3. Freely branching habit and short internodes; dense and busy plant habit.
4. Freely and continuous flowering habit.
5. Bright purple violet-colored flowers.
6. Relatively tolerant to high temperatures.
7. Relatively resistant to Powdery Mildew.

Plants of the new *Phlox* can be compared to plants of the parent selections. Plants of the new *Phlox* differ from plants of the female parent selection in the following characteristics:

1. Plants of the new *Phlox* are more freely branching than plants of the female parent selection.
2. Plants of the new *Phlox* and the female parent selection differ in flower color as plants of the female parent selection have white-colored flowers.

Plants of the new *Phlox* differ from plants of the male parent selection in the following characteristics:

1. Plants of the new *Phlox* are more vigorous than plants of the male parent selection.
2. Plants of the new *Phlox* and the male parent selection differ in flower color as plants of the male parent selection have white-colored flowers.

Plants of the new *Phlox* can be compared to plants of the *Phlox* 'USPHLO322', disclosed in U.S. Plant Pat. No. 17,894. In side-by-side comparisons, plants of the new *Phlox* and 'USPHLO322' differed in the following characteristics:

1. Flower petals of plants of the new *Phlox* were more serrated and pointed than flower petals of plants of 'USPHLO322'.
2. Plants of the new *Phlox* and 'USPHLO322' differed slightly in flower coloration.

Plants of the new *Phlox* can also be compared to plants of the *Phlox* 'Sunphlorozu', disclosed in U.S. Plant patent application Ser. No. 12/383,283. In side-by-side comparisons, plants of the new *Phlox* and 'Sunphlorozu' differed in the following characteristics:

1. Flower petals of plants of the new *Phlox* were more serrated and pointed than flower petals of plants of 'Sunphlorozu'.
2. Plants of the new *Phlox* and 'Sunphlorozu' differed in flower coloration.

3. Plants of the new *Phlox* were more resistant to Powdery Mildew than plants of 'Sunphlorozu'.

BRIEF DESCRIPTION OF THE PHOTOGRAPHS

The accompanying colored photographs illustrate the overall appearance of the new *Phlox* plant, showing the colors as true as it is reasonably possible to obtain in colored reproductions of this type. Colors in the photographs may differ slightly from the color values cited in the detailed botanical description which accurately describe the colors of the new *Phlox* plant.

The photograph at the bottom of the sheet comprises a side perspective view of a typical flowering plant of 'USPLX50304' grown in a container.

The photograph at the top of the sheet is a close-up view of typical flowers and leaves of 'USPLX50304'.

DETAILED BOTANICAL DESCRIPTION

The aforementioned photographs and following observations, measurements and values describe plants grown in Bonsall, Calif., under commercial practice in one-gallon containers during the autumn in an outdoor nursery with day temperatures ranging from 18° C. to 38° C., night temperatures ranging from 9° C. to 18° C. and light levels ranging from 7,000 to 10,000 foot-candles. Plants were pinched one time and were 74 days old when the photographs and description were taken. In the following description, color references are made to The Royal Horticultural Society Colour Chart, 2007 Edition, except where general terms of ordinary dictionary significance are used.

Botanical classification: *Phlox hybrida* 'USPLX50304'.

Parentage:

*Female, or seed, parent.*—Unnamed selection of *Phlox glabriflora,* not patented.

*Male, or pollen, parent.*—Unnamed seedling selection of *Phlox hybrida,* not patented.

Propagation:

*Type.*—By cuttings.

*Time to initiate roots, summer.*—About six days at temperatures ranging from 17° C. to 29° C.

*Time to initiate roots, winter.*—About four days at temperatures ranging from 17° C. to 21° C.

*Time to produce a rooted plant, summer.*—About 28 days at temperatures ranging from 17° C. to 29° C.

*Time to produce a rooted plant, winter.*—About 25 days at temperatures ranging from 17° C. to 21° C.

*Root description.*—Fine to medium in thickness; white in color.

*Rooting habit.*—Moderate branching; sparse to medium in density.

Plant description:

*Plant form/habit.*—Upright, outwardly spreading and mounding plant form; vigorous growth habit; freely branching habit, about twelve main laterals each with numerous secondary laterals; relatively short internodes; dense and bushy plant habit.

*Plant height.*—About 20 cm.

*Plant width (spread).*—About 38 cm.

*Lateral branches.*—Length: About 16 cm. Diameter: About 2.5 mm. Internode length: About 1.2 cm. Strength: Strong. Texture: Pubescent. Color: Close to 146B.

Foliage description:

*Arrangement.*—Alternate, simple; sessile.

*Length.*—About 2.6 cm.

*Width.*—About 1 cm.

*Shape.*—Oblanceolate to narrowly deltoid.

*Apex.*—Acute.

*Base.*—Rounded to slightly auriculate; clasping.

*Margin.*—Entire.

*Texture, upper and lower surfaces.*—Pubescent.

*Venation pattern.*—Pinnate.

*Color.*—Developing and fully expanded leaves, upper surface: Close to 146A; venation, close to 146B. Developing and fully expanded leaves, lower surface: Close to 146B; venation, close to 146C.

Flower description:

*Flower type/habit.*—Single rotate and salverform flowers arranged in small cymes of four to six flowers each; flowers face upright to outwardly; freely flowering habit with about 100 flower buds and flowers developing per plant.

*Fragrance.*—Faint; vanilla-like.

*Natural flowering season.*—Continuously flowering from spring to frost in California.

*Postproduction longevity.*—Flowers last about five days on the plant; flowers persistent.

*Flower buds.*—Height: About 1.7 cm. Diameter: About 5 mm. Shape: Obovate. Color: Close to 85D.

*Inflorescence height.*—About 3.4 cm.

*Inflorescence diameter.*—About 4.5 cm to 6 cm.

*Flower diameter.*—About 2.8 cm.

*Flower depth.*—About 2.3 cm.

*Flower throat diameter.*—About 3 mm.

*Flower tube length.*—About 1.4 cm.

*Flower tube diameter, at base.*—About 2 mm.

*Petals.*—Quantity per flower: Typically five in a single whorl; petals fused at the base into a narrow tube. Lobe length: About 1.2 cm. Lobe width: About 1.1 cm. Shape: Obovate. Apex: Rounded, erose. Margin: Entire. Texture: Petal lobes, upper surface: Smooth, glabrous; velvety. Petal lobes, lower surface: Smooth, glabrous; satiny. Throat: Smooth, glabrous. Tube: Pubescent. Color: Developing petals, upper surface: Close to N81C. Developing petals, lower surface: Close to 85D. Fully expanded petals, upper surface: Close to N81C; star-shaped central pattern, close to N74A; circle surrounding throat, close to 68B; color becoming closer to N78C to N78D with development; venation, close to N81C. Fully expanded petals, lower surface: Close to 85C to 85D; venation, close to 85D. Flower throat: Close to N78D; venation, close to N78D. Flower tube: Close to 84C; venation, close to 84B.

*Sepals.*—Quantity per flower: Typically five in a single whorl, fused towards the base into a slender tube and reflexed towards the apex. Length: About 6 mm. Width: About 1 mm. Shape: Lanceolate. Apex: Acuminate. Margin: Entire. Texture, upper and lower surfaces: Pubescent. Color, upper and lower surfaces: Close to 144A.

*Peduncles.*—Length: About 1 cm. Diameter: About 2 mm. Angle: Erect to about 45° from vertical. Strength: Strong. Texture: Pubescent. Color: Close to 144B.

*Pedicels.*—Length: About 6 mm. Diameter: About 1.5 mm. Angle: Erect to about 30° to about 40° from peduncle axis. Strength: Strong. Texture: Pubescent. Color: Close to 144C.

*Reproductive organs.*—Stamens: Quantity per flower: Typically five. Filament length: About 1 mm. Filament color: Close to 157D. Anther shape: Narrowly oblong. Anther length: About 2 mm. Anther color: Close to 12A. Pollen amount: Scarce to moderate. Pollen color: Close to 14B. Pistils: Quantity per flower: One. Pistil length: About 5 mm. Stigma shape: Three-parted. Stigma color: Close to 145C. Style length: About 1.5 mm. Style color: Close to 145B. Ovary color: Close to 144A.

*Seed/fruit.*—Seed and fruit development have not been observed.

Disease/pest resistance: Plants of the new *Phlox* have been noted to be relatively resistant to Powdery Mildew. Plants of the new *Phlox* have not been noted to be resistant to pests and other pathogens common to *Phlox*.

Garden performance: Plants of the new *Phlox* have been observed to have good garden performance and tolerate rain, wind and temperatures ranging from about 1° C. to about 40° C.; relatively tolerant to high temperatures.

It is claimed:

1. A new and distinct *Phlox* plant named 'USPLX50304' as illustrated and described.

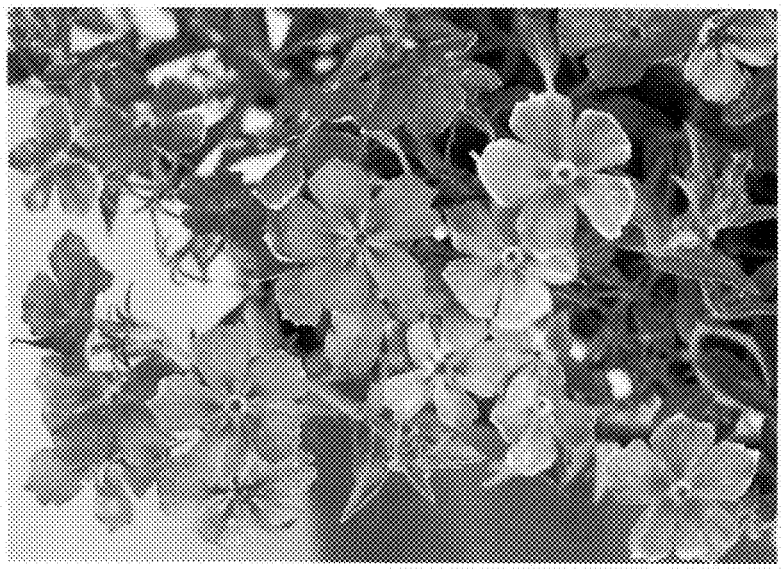
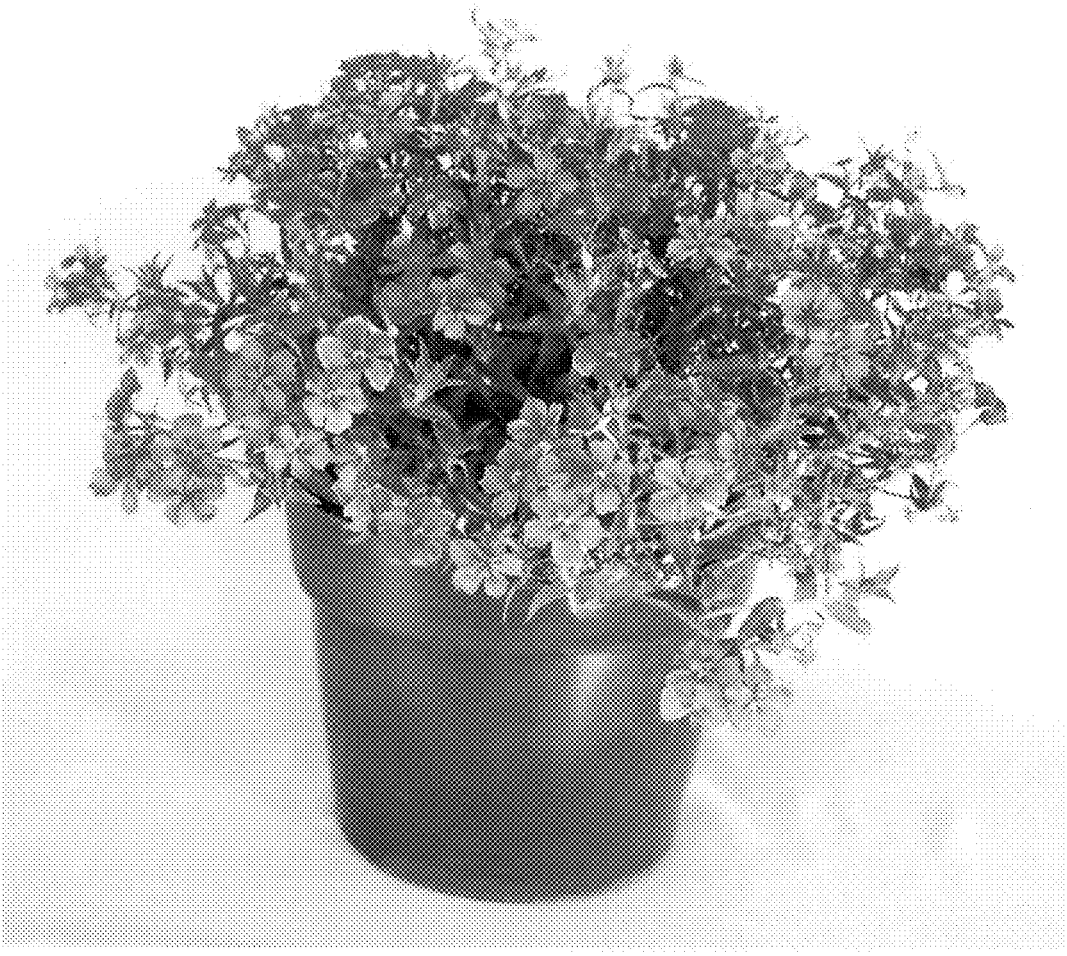

* * * * *